United States Patent [19]

Baggiolini et al.

[11] 3,957,794

[45] May 18, 1976

[54] 3-AMINO-2,3,3A,6,7,7A-HEXAHYDRO-THIENO[3,2-B]PYRIDIN-(4H)5-ONE

[75] Inventors: Enrico Baggiolini, Nutley; Pasquale Nicholas Confalone, Bloomfield; Giacomo Pizzolato, Belleville; Milan Radoje Uskokovic, Upper Montclair, all of N.J.

[73] Assignee: Hoffmann-La Roche Inc., Nutley, N.J.

[22] Filed: May 2, 1975

[21] Appl. No.: 574,080

[52] U.S. Cl. ............... 260/293.55; 260/306.7 C; 260/309.7; 260/332.2 A
[51] Int. Cl.$^2$ ............................................. C07D 333/00
[58] Field of Search ............................. 260/293.55

[56] References Cited
UNITED STATES PATENTS 3,632,592   1/1972   Nakanishi et al. ............ 260/294.8 C

OTHER PUBLICATIONS

Ali et al., Carbohyd. Res. 5 (4), 441–448 (1967).
Boyer, J. Am. Chem. Soc., 73, 5865–5866 (1951).
Boyer et al., J. Org. Chem., 23, 127–129 (1958).
Coffey, "Rodds' Chemistry of Carbon Compounds, Vol. I, Part B, Second Edition," Elsevier, New York (1965), p. 162.

*Primary Examiner*—G. Thomas Todd
*Attorney, Agent, or Firm*—Samuel L. Welt; Bernard S. Leon; Richard A. Gaither

[57] ABSTRACT

A novel procedure for the preparation of biotin, using cysteine as the starting material is disclosed. This process results in the obtention of pure d-biotin thus obviating the need for a chemical resolution. Novel intermediates are also disclosed.

1 Claim, No Drawings

3-AMINO-2,3,3A,6,7,7A-HEXAHYDRO-THIENO[3,2-B]PYRIDIN-(4H)5-ONE

BACKGROUND OF THE INVENTION

This invention relates to a process of preparing biotin from L-(+)-cysteine. Biotin, vitamin H, is a natural product found largely in the kidney, liver, egg yolk, milk and yeast. The compound is used to prevent symptoms of egg-white injury in experimental animals. Its prime medical use is in various dematitides.

Biotin has been prepared synthetically by Harris et al. (Science, 97, 447 (1943) and Baker et al. (J. Org. Chem., 12, 167 (1947), among others. None of these syntheses, however, were commercially feasible. The first commercial synthesis of biotin resulted from the work of Goldberg and Sternbach (U.S. Pat. Nos. 2,489,235 and 2,489,236).

Previous biotin syntheses suffer from the disadvantages that racemic mixtures of intermediates, as well as racemic mixtures of biotin, are formed thus requiring costly and time consuming resolutions. These resolutions also lead to decreased yields of biotin. This disadvantages is obviated in the instant invention by use of cysteine as the starting material. Cysteine, a natural amino acid is an optically active compound with the same absolute configuration as the $C_4$-carbon of d-biotin, the biologically active form of biotin. The process of the instant invention proceeds without racemization in forming d-biotin, thus obviating the need for resolution of the final product.

According to the instant invention, biotin is obtained in the optically pure d-form from a relatively inexpensive starting material, thus avoiding the costly and inefficient chemical resolutions heretofore required.

SUMMARY OF THE INVENTION

This invention is directed to a process for synthesizing d-biotin, which has the structural formula:

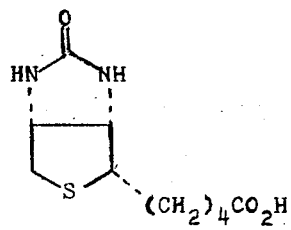

from cysteine, a compound of the formula:

$$\begin{array}{c} NH_2 \\ | \\ H\blacksquare\!-\!-\!CO_2H \\ | \\ SH \end{array} \quad I$$

DETAILED DESCRIPTION OF THE INVENTION

The term "aliphatic" as used herein, denotes straight or branched chain hydrocarbon groups of 1 to 20 carbon atoms which are saturated or which include one or more double and/or triple carbon to carbon bonds, such as methyl, ethyl, allyl, propargyl, hexenyl and decyl. The term "cycloaliphatic" denotes monocyclic groups of 3 to 7 carbon atoms and polycyclic groups of 5 to 17 carbon atoms, which are saturated or which contain double and/or triple carbon to carbon bonds, such as menthyl, bornyl and cholesteryl.

As further used throughout this application, the term "lower alkyl" denotes straight chain and branched chain saturated aliphatic groups having from 1 to 8 carbon atoms, such as methyl, ethyl, propyl, isopropyl, butyl, isobutyl and the like. As also used herein, the term "aryl" signifies mononuclear aromatic groups, such as phenyl, which can be unsubstituted or substituted in one or more positions with a lower alkylenedioxy, a halogen, a nitro, a lower alkyl or a lower alkoxy substituent and polynuclear aryl groups of 10 to 17 carbon atoms, such as naphthyl, anthryl, phenanthryl and azulyl, which can be substituted with one or more of the aforementioned groups. The preferred aryl groups are the substituted and unsubstituted mononuclear aryl groups, particularly phenyl. As further used herein, the term "aryl lower alkyl" comprehends groups wherein aryl and lower alkyl are as defined above, particularly benzyl. As still further used herein, the term "lower alkoxy" comprehends alkoxy groups having from 1 to 7 carbon atoms such as methoxy, ethoxy and the like. Also herein, the term "halogen" or "halo", unless otherwise stated, comprehends fluorine, chlorine, bromine and iodine. Further herein, the term "lower alkylenedioxy" comprehends lower alkylenedioxy groups having 1 to 4 carbon atoms, such as methylenedioxy and ethylenedioxy.

As still further used throughout this application, in the pictorial representations of the compounds of this application, a thickened tapered line (■) indicates a substituent which is in the β-orientation (above the plane of the molecule), a dotted line (---) indicates a substitutent which is in the α-orientation (below the plane of the molecule) and a wavy line (~) indicates a substituent which is in either the α- or β-orientation.

In accordance, with the instant invention, d-biotin is prepared from cysteine in conformity with the following scheme:

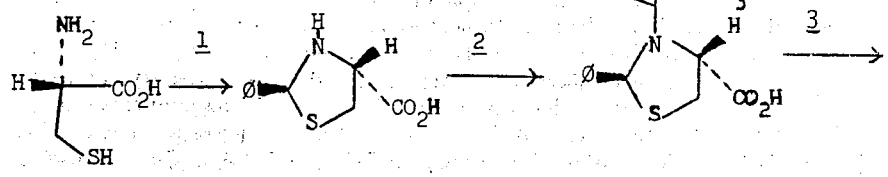

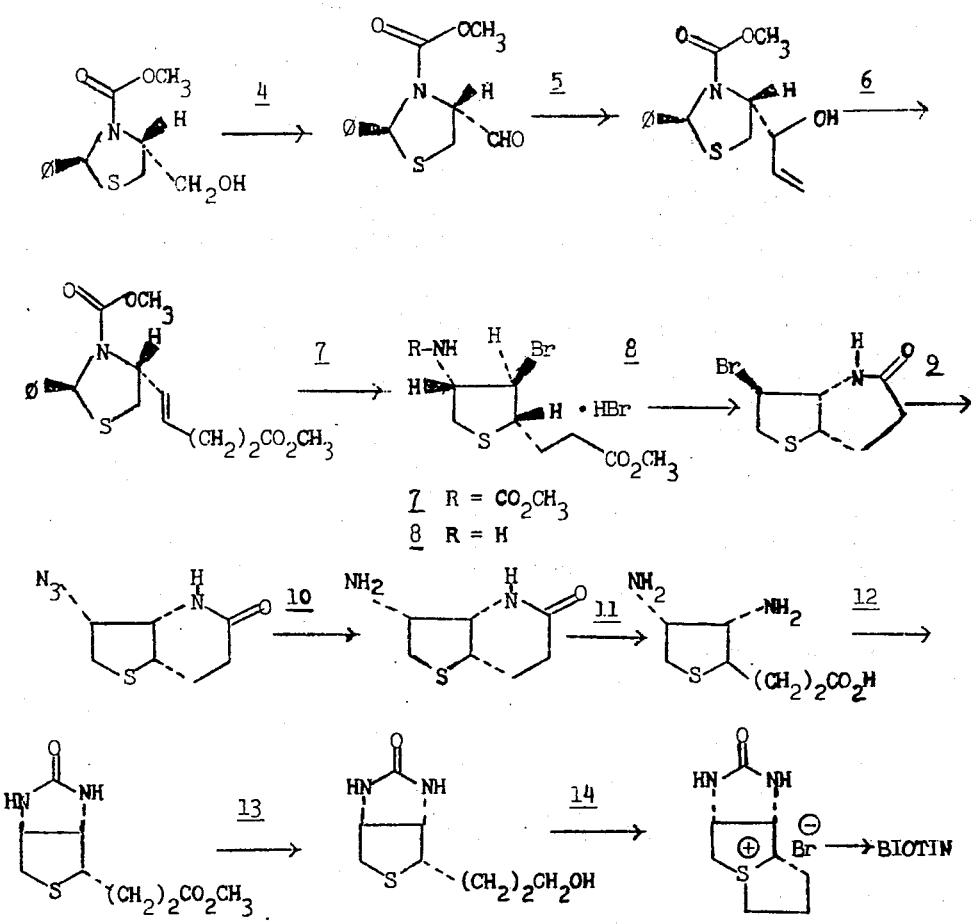

D-biotin is obtained by first converting L-(+)-cysteine to a compound having the formula:

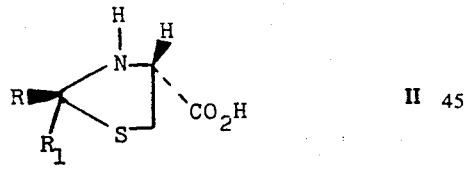
II wherein R and R₁ are hydrogen, lower alkyl, substituted or unsubstituted aryl, aryl(lower)alkyl.

In carrying out the reaction, L-(+)-cysteine is treated in the presence of a weak alkali or alkaline earth metal base with a lower alkyl or aromatic aldehyde or ketone. The reaction is carried out at a pH of about 4–5 in alcoholic solvents. Temperature and pressure are not critical but the reaction is preferably carried out at room temperature and atmospheric pressure. The alcoholic solvents are generally lower alkanols such as methanol, ethanol, propanol, isopropanol, butanol, isobutanol, t-butanol and the like. Typical weak bases that they may be employed are the alkali or alkaline earth metal salts of lower alkyl carboxylic acids with potassium acetate beingn particularly preferred.

The reaction of cysteine with alkyl or aromatic aldehydes or ketones serves to mask or protect the amino and mercapto groups. Typical aldehydes and ketones that mav be employed are formaldehyde, acetaldehyde, propionaldehyde, butyraldehyde, benzaldehyde, phenylacetaldehyde, acetone, methyl ethyl ketone, methyl isopropyl ketone, acetophenone and the like.

Compound II is then converted to a compound of the formula:

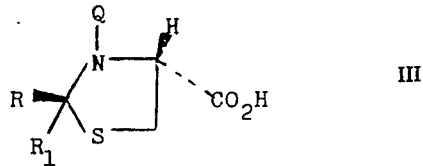
III wherein R and R₁ are as defined above and Q is a protecting group selected from the group consisting of —CO₂R₂,

wherein R₂ is lower alkyl, substituted or unsubstituted aryl, aryl(lower)alkyl, tosyl or mesyl.

This conversion occurs by treating compound II with a lower alkyl acid anhydride, an acyl halide, or a halogenated ester of formic acid. The reaction takes place under basic conditions, generally a pH of about 8–10 will suffice. Temperature and pressure are not critical, but generally room temperature and atmospheric pressure are employed. The reaction may be conducted in the presence or absence of solvent. If a solvent is employed, typically inert solvents such as ether, benzene, toluene and the like are used.

Compound III, which is novel and forms another aspect of this invention, is prepared by reacting compound II with a compound of the formula QX, wherein Q is as defined above and X is chlorine or bromine, in the presence of a base. When Q is acyl, typical acid halides that may be employed are acetyl chloride, propionyl chloride, n-butyryl chloride and the like. The bromo, fluoro and iodo derivatives may also be used. When Q is a halogenated ester of formic acid, compounds such as methyl chloroformate, ethyl chloroformate, isopropyl chloroformate, phenyl chloroformate, benzyl chloroformate and the like may be employed. The bromo and iodo derivatives may also be employed. Especially preferred as methyl chloroformate. Typical bases that may be employed are sodium bicarbonate, potassium bicarbonate, sodium hydroxide, potassium hydroxide, ammonium hydroxide and the like.

Compound III is then converted to a compound of the formula:

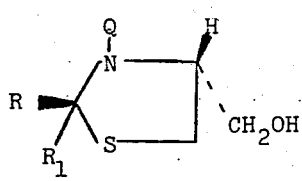

IV wherein R, $R_1$ and Q are as defined above.

Compound IV is novel and forms yet another aspect of this invention.

The conversion of compound III to compound IV is accomplished by reduction. The reduction may be carried out according to either of two procedures. The first, and most preferred procedure is the direct reduction of compound III with diborane. An alternative procedure involves the formation of a mixed lower alkyl acid anhydride of compound III followed by reduction with sodium borohydride. More specifically, compound III is reacted with a lower alkyl haloformate to form a compound having the formula:

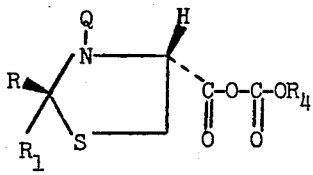

IIIa wherein R, $R_1$ and Q are as previously defined; and $R_4$ is lower alkyl;
followed by treatment with $NaBH_4$ to form compound IV. Lower alkyl chloroformates are preferred. Methyl and ethyl chloroformates are particularly preferred. Temperatures and pressure are not critical but the reaction is generally carried out at room temperature and atmospheric pressure. The reaction generally is conducted in an inert solvent such as diethyl ether or tetrahydrofuran.

Compound IV is then converted to a compound of the formula:

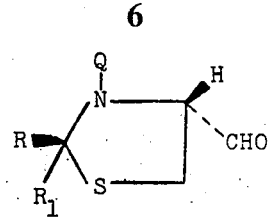

V wherein Q, R and $R_1$ are as previously defined.

Compound V is novel and forms still another aspect of this invention. Compound IV is converted to compound V by oxidation using conventional oxidizing agents such as dimethylsulfoxide-dicyclohexyl carbodiimide, dimethylsulfoxide/ acetic anhydride and $CrO_3$/-pyridine. $CrO_3$/ pyridine is particularly preferred. Temperature and pressure are not critical but room temperature and atmospheric pressure are preferred. The reaction is generally carried out in an inert solvent. Typical inert solvents that may be employed are methylene chloride, benzene, toluene, diethyl ether and the like. This conversion is especially surprising in that the sulfur atom present in the molecule is not oxidized or in any way affected during the course of the reaction. This is advantageous in that it allows for selective oxidation of the hydroxymethylene substituent of compound IV.

Compound V is then converted to a compound of the formula:

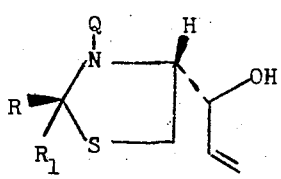

VI wherein Q, R and $R_1$ are as previously defined.

Compound VI is novel and forms a further aspect of the instant invention. Compound VI is formed by treating compound V with a vinyl organometallic compound or an organolithium compound, preferably a vinyl magnesium halide or a vinyl lithium compound. The reaction takes place at atmospheric pressure and at a temperature of from about −80° to about 0°C., preferably −60° to about −70°C. This reaction may be carried out in the presence of solvents such as methylene halides, e.g., methylene chloride and haloforms, e.g., chloroform. A surprising aspect of this reaction is that the Q moiety of compound V survives. This is especially surprising in view of the fact that Grignards and organolithium compounds readily react with carbonyl groups. This is advantageous in that there is no need to introduce additional protective groups to the thiazolidine ring.

Compound VI is then transformed to a compound of the formula:

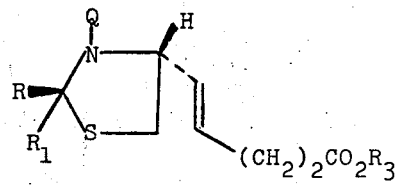

VII wherein R, $R_1$ and Q are as previously defined, and $R_3$ is hydrogen or lower alkyl.

Compound VII is novel and forms still a further aspect of this invention.

Compound VI is reacted with a triloweralkyl ester of ortho acetic acids, e.g., trimethyl orthoacetate, in the presence of an acid catalyst. Typical acids employed as catalysts are lower alkyl monocarboxylic acids such as acetic, propionic, butyric acids and the like. Other acids that may be employed as catalysts are phosphoric, oxalic o-nitrobenzoic acid, p-nitrophenol, and perchlorohomocubane carboxylic acid. The reaction between compound VI and the ortho acid ester results in an intermediate having the formula:

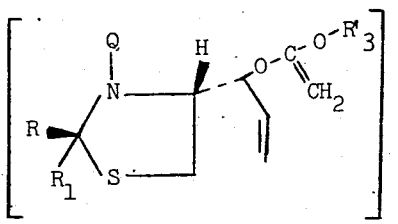

VIa wherein R, R$_1$ and Q are as previously defined and R'$_3$ is lower alkyl.

Compound VIa then undergoes a Claisen rearrangement to form compound VII. The reaction takes place at atmospheric pressure and at a temperature of from about 50° to about 150°C., preferably from about 85°–95°C. The reaction may be carried out in the presence or absence of conventional organic solvents. Typical solvents that may be employed are benzene, toluene, ethylbenzene and the like.

The double bond formed in the side chain is exclusively trans wthout a trace of the cis isomer. This is highly desirable because the presence of a cis double bond in the side chain leads to the obtention of epi-biotin rather than the desired d-biotin.

Compound VII is then converted to a compound having the formula:

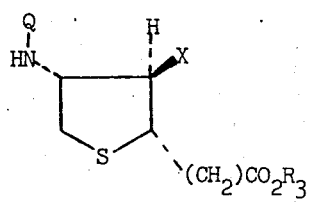

VIII wherein Q and R$_3$ are as previously defined and X is chlorine or bromine.

Compound VIII is novel and forms an additional aspect of this invention. Compound VIII is formed by halogenating compound VII, which halogenation results in a cleavage and rearrangement yielding a tetrahydrothiophene. The tetrahydrothiophene possesses the ideal structure for further elaboration to biotin. Furthermore, only one of the possible diastereroisomers is obtained in this step. No trace of the other possible diastereoisomers is obtained. The halogen employed may be either chlorine or bromine, with bromine being preferred. Bromine is preferably employed as a hydrobromide/perbromide complex, especially the pyridine hydrobromide perbromide.

The reaction may take place in conventional solvents such as lower alkanols, and halogenated hydrocarbon. Typical solvents that may be used include methanol, ethanol, propanol, isopropanol, butanol, methylene chloride, chloroform and the like. Methanol is particularly preferred. The reaction is generally carried out at atmospheric pressure and a temperature of about −20° to about 80°C.

Compound VIII is then transformed to a compound having the formula:

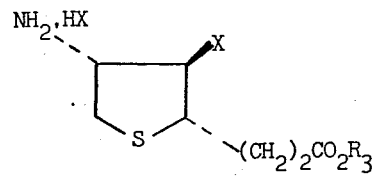

IX wherein X and R$_3$ are as previously defined.

Compound IX is novel and an additional aspect of the instant invention. Compound VIII is converted to compound IX by treating the former with a saturated mixture of a hydrohalic acid and a lower alkyl monocarboxylic acid. Hydrohalic acids that may be employed are HCl, HBr, and HI, preferably HBr. The lower alkyl monocarboxylic acids that may be employed are acids such as acetic, propionic, butyric and the like. Acetic acid is particularly preferred. The reaction generally takes place at atmospheric pressure and room temperature, although these parameters are not critical.

The surprising aspect of this reaction is that it proceeds without hydrolysis of the ester side chain.

Compound IX is then converted to a compound having the formula:

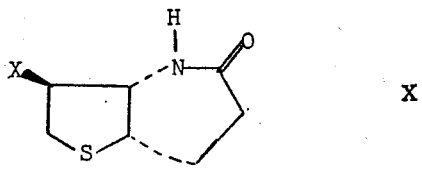

X wherein X is as previously defined.

Compound X is novel, forming an additional aspect of the instant invention.

Compound X is formed by treating compound IX with a mixture of an alkali or alkaline earth metal salt of a lower alkyl monocarboxylic acid and a lower alkyl monocarboxylic acid. The aforementioned alkali or alkaline earth metal salts that may be employed are sodium, potassium, lithium, calcium or magnesium salts. The lower alkyl monocarboxylic acids may be acids such as acetic, propionic, butyric and the like. Especially preferred is a mixture of sodium acetate in acetic acid. The reaction is carried out at atmospheric pressure and temperatures from about 85° to about 150°C., preferably at reflux conditions.

The advantage of this reaction is that it results in a rearrangement of the halogen moiety and the nitrogen moiety, in a completely stereospecific reaction. The nitrogen moiety is now in the desired configuration for the ultimate biotin product.

Compound X is then converted to a compound having the formula:

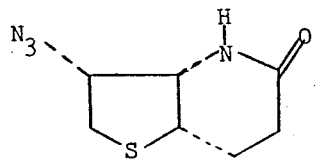

XI

Compound XI is a novel compound forming another aspect of this invention.

Compound XI is formed by treating compound X with an alkali metal azide in the presence of an aprotic inert solvent. Typical solvents that may be employed are dimethylformamide (DMF), tetramethylurea, hexamethylphosphoric acid triamide, aniline, dimethylaniline, pyridine, triethylamine and the like. The alkali metals that may be employed are sodium, potassium, and lithium. The reaction is conducted at atmospheric pressure and at a temperature of from about 80° to about 180°C., preferably at about 110° to about 140°C.

Compound XI is subsequently converted to a compound of the formula:

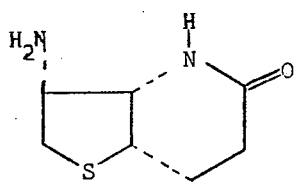

XII

Compound XII is novel forming yet another aspect of this invention.

Compound XII is formed by the chemical reduction or catalytic hydrogenation of compound XI. The hydrogenation is carried out with conventional supported or unsupported hydrogenation catalysts. Typical hydrogenation catalysts may be employed are platinum, palladium, Raney nickel, and Raney cobalt. Especially preferred is palladium on a carbon support. The hydrogenation is carried out at temperatures from room temperature to 150°C. and at pressures of from about 1 psig to 50 psig, preferably 35–45 psig. Chemical reducing agents that may be employed are Al/Hg in methanol, alkali metal borohydrides such as sodium and lithium borohydrides, zinc metal, iron, and stannous chloride in the presence of strong acids. Examples of strong acids are HCl, HBr, HI, $H_2SO_4$, $HNO_3$, $H_3PO_4$, chloroacetic, trichloroacetic acid and the like.

The hydrogenation or chemical reduction may be carried out in inert solvents such as hexane, heptane, benzene, toluene, diethyl ether, tetrahydrofuran and the like.

Compound XII is then converted to a compound having the formula

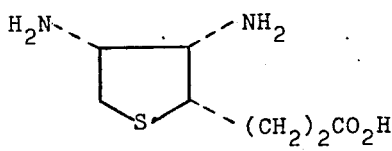

XIII

Compound XIII which is novel, thus forming another aspect of this invention, is obtained by the treatment of compound XII with an alkali metal or alkaline earth metal hydroxide base in aqueous solution. Typical bases that may be employed are sodium, potassium and lithium hydroxides, barium, calcium and magnesium hydroxides. The reaction is carried out at pressures of from 1–10 atmospheres and temperatures of from 100° to 200°C. Temperatures and pressures are not critical, however.

Compound XIII is then transformed into a compound of the formula:

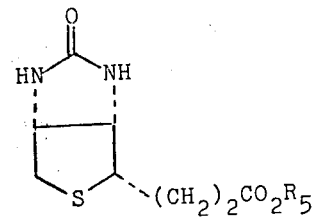

XIV wherein $R_5$ is lower alkyl.

Compound XIV is obtained by treating compound XIII first with a compound of the formula:

XVII wherein Y is halogen or lower alkoxy;
followed by treatment with a lower alkanol and a mineral acid. Typical compounds within the scope of formula XVII that may be employed are lower alkyl halocarbonates such as as methylhalo, ethylhalo, propylhalo carbonates, dimethyl, diethyl, dipropyl carbonates, carbonyl bromide, carbonyl iodide and carbonyl chloride (phosgene). Phosgene is preferred. Typical lower alkanols that may be employed are methanol, ethanol, propanol, isopropanol and the like. Mineral acids that may be employed are sulfuric, hydrochloric, nitric and the like. This reaction is carried out at a pressure of 1–10 atmospheres and a temperature of from 50° to about 150°C.

The formation of compound XIV may be accomplished stepwise as described above or compound XIV may be prepared directly from compound XII. Rather than isolating compound XIII, all that need to be accomplished is removal of the barium by-product and subsequently treating XIII with compound XVII, mineral acid, etc. as described hereinbefore.

Compound XIV is transformed to a compound of the formula:

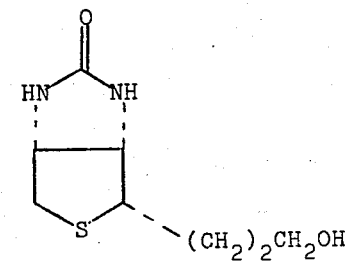

XV

Compound XV is novel forming another aspect of the invention.

Compound XV is obtained by the reduction of compound XIV. To accomplish the reduction, conventional reducing agents are employed. Exemplary of the reducing agents are LiBH$_4$, B$_2$H$_6$, NaBH$_4$ and the like. The reduction is carried out at room temperature and atmospheric pressure although these parameters are not critical.

Compound XV is transformed into a compound of the formula:

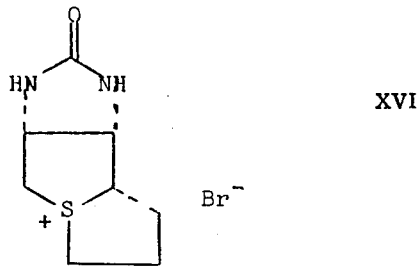

XVI

The transformation of compound XV to compound XVI is accomplished by treating compound XV with a saturated mixture of a hydrohalic acid and a lower alkyl monocarboxylic acid. The reaction conditions and reactant materials are the same as those employed for the transformation of compound VIII to compound IX described hereinbefore.

Compound XVI is converted to d-biotin by treatment with a solution of an an alkali or alkaline earth metal in a di(lower)alkyl malonate followed by treatment with aqueous base according to the procedure of Goldberg et al., U.S. Pat. No. 2,489,235. The temperature employed may be from about 70° to about 150°C. at pressures of from 1 to 10 atmospheres. Typical bases that may be employed are aqueous solutions of sodium and potassium hydroxide, calcium, magnesium and barium hydroxide. A preferred base is the octahydrate of barium hydroxide.

The alkali metals that may be employed are sodium, potassium or lithium, with sodium being preferred. The alkaline earth metals that may be employed are calcium, magnesium and barium.

The d-3,4-(2'-ketoimidazolido)-2-($\omega$,$\omega$-dicarboxybutyl)-thiophane formed from the thiophanium bromide is decarboxylated by heating an aqueous solution under pressure to form biotin. The reaction is carried out at a temperature of from about 175°–195°C., preferably 180°C. and a pressure of from 1 to 5 atmospheres.

In view of the fact that compounds III–XIII and XV, disclosed and claimed herein, are optically active, it is to be understood that their racemates and optical antipodes are included herein.

The examples which follow illustrate the invention. All temperatures are in degrees Centigrade.

EXAMPLE 1

To a solution of 60 g. (0.342 mole) of L-(+)-cysteine hydrochloride hydrate in 525 ml. of water was added 36 g. (0.368 mole) of potassium acetate. After the reactants dissolved, 525 ml. of 95% ethanol was added followed immediately by 42 ml. (44.2 g., 417 mole) of benzaldehyde (added in one portion). After about 15 minute, the product began to crystallize. The reaction mixture was allowed to stand for 3 hours at 25° and finally for 3 hours at 0°. At this point, the product is filtered, washed with 95% ethanol, dried in vacuo overnight to afford 72 g. (98%) of 2-phenyl-4-(R)-carboxythiazolidine, having a m.p. 159°–160°.

EXAMPLE 2

To a mixture of 60 g. of sodium carbonate in 330 ml. of water and 220 ml. of 10% sodium bicarbonate was added 62.7 g. (.3 mole) of 2-phenyl-4-(R)-carboxythiazolidine. A solution of 23.0 ml. (28.4 g., 0.3 mole) of methyl chloroformate in 75 ml. of ether was added dropwise over 30 minutes. The reaction mixture was stirred at room temperature for one additional hour. The entire reaction mixture, including some solid which occasionally separated, was acidified carefully (foaming) to pH 1 by the dropwise addition of about 50 ml. of 6N HCl. The reaction was extracted 3 × 300 ml. portions of methylene chloride. The organic phases were dried over sodium sulfate and evaporated to afford 77.4 g (97%) of the 2-phenyl-3-carbomethoxy-4-(R)-carboxythiazolidine as a white crystalline solid, having a m.p. of 129°–130°C.

Calcd for C$_{12}$H$_{13}$NO$_4$S: Calcd: C, 54.00; H, 4.87; N, 5.25; S, 11.98. Found: C, 54.03; H, 4.94; N, 5.27; S, 11.63.

EXAMPLE 3

To a solution of 80.0 g (.300 mole) of 2-phenyl-3-carbomethoxy-4-(R)-carboxythiazolidine in 150 ml. of dry tetrahydrofuran was added dropwise 400 ml. (.4 mole) of diborane as a 1 molar solution in tetrahydrofuran. After the addition was complete, the reaction was allowed to proceed at room temperature for 30 minutes. The reaction was then quenched with 800 ml. of water. The mixture was further diluted with 300 ml. of 10% sodium bicarbonate and extracted with 3 × 400 ml. portions of methylene chloride. The organic phases were dried over sodium sulfate and evaporated to afford 75.0 g. (99%) of 2-phenyl-3-carbomethoxy-4-(R)-hydroxymethylthiazolidine as a white crystalline solid, having a m.p. of 85°–86°.

Calcd. for C$_{12}$H$_{13}$NO$_3$S: Calcd: c, 56.90; H, 5.97; N, 5.53; S, 12.66. found: C, 56.71; H, 5.79; N, 5.79; S, 12.41.

EXAMPLE 4

To a mixture of 1200 ml. of dry methylene chloride and 77.6 ml. of dry pyridine was added 48 g. (0.48 mole) of chromium trioxide (mechanical stirring). After 15 minutes at room temperature, the reaction mixture was treated in one portion with a solution of 20.24 g. (0.08 mole) of 2-phenyl-3-carbomethoxy-4-(R)-hydroxymethylthiazolidine in 50 ml. of dry methylene chloride. A dark resinous material immediately separated. The reaction was allowed to proceed for 15 minutes at room temperature. The supernatant was decanted and the reaction flask was washed with 3 × 200 ml. portions of methylene chloride. The washings were combined with the supernatant and the mixture was evaporated. The residue was then triturated with 3 × 200 portions of ether. The ether phases were combined and washed with 1 × 200 ml. portions of 1N HCl until the pH of the aqueous phase was equal to 1. Following a final wash of the ether phase with 200 ml. of water, the organic layer was dried over magnesium sulfate, filtered and evaporated to afford 16.0 g. (80%)

of 2-phenyl-3-carbomethoxy-4-(R)-formylthiazolidine as a colorless, viscous oil, pure by tlc.

EXAMPLE 5

To a mixture of 310 ml. (0.440 mole) of vinylmagnesium chloride (from Ventron Corp., 1.42 molar in tetrahydrofuran) and 250 ml. of methylene chloride, which had been previously prepared and kept at −74°C., a solution of 14.2 g. (0.0565 mol) of 4-formyl-3-carbomethoxy-2-phenylthiazolidine dissolved in 50 ml. of methylene chloride was added over a period of 7–10 minutes, while the temperature of the reaction was kept at −60° to −70°C. After addition, the reaction mixture was stirred for 30 minutes at the same temperature while 30 ml. of methanol were slowly added, followed by addition of 150 ml. of saturated ammonium chloride. When the addition was finished, the mixture was allowed to reach room temperature and extracted with 3 × 300 ml. of methylene chloride. The combined organic phases were washed with 2 × 200 ml. of water, dried with sodium sulfate, and evaporated to give 13.7 g. (87% yield) of crude 4-(1-hydroxyprop-2-en-1-yl)-3-carbomethoxy-2-phenylthiazolidine which was obtained as thick oil. This contains a small amount of starting material which, for future separation purposes, is convenient to convert into its corresponding alcohol. To this end, the crude product, dissolved in 100 ml. of tetrahydrofuran was slowly added to a solution of 0.9 g. (0.0503 mol) of sodium borohydride in 75 ml. of water and 75 ml. of tetrahydrofuran. After addition, the resulting yellow emulsion was stirred for 2 hours at room temperature. 55 ml. of 1N hydrochloric acid were then slowly added, the tetrahydrofuran removed in vacuo and the residue extracted with 3 × 100 ml. of ethyl acetate. The combined organic phases were washed with 100 ml. of 5% sodium bicarbonate solution and finally with 2 × 100 ml. of water. Drying with magnesium sulfate and evaporating the solvent gave 13.0 g. of the desired product, which can be used as such for the further transformations or it can be further purified by chromatography on silica gel, using benzene/ethyl acetate (1:1) as eluent. 4.1 g. (corresponding to a yield of 26% from a starting material) of very pure product was obtained as pale yellow thick oil.

Calcd for $C_{12}H_{17}NO_3S$ (279.36): Calcd: C, 60.19; H, 6.13; N, 5.01; S, 11.18. Found: C, 59.88; H, 6.25 N, 4.92; S, 11.08.

EXAMPLE 6

A solution of 44.0 g. (0.1575 mol) of crude 4-(1-hydroxyprop-2-en-1-yl)-3-carbomethoxy-2-phenylthiazolidine, 191.5 g. (1.570 mol) of trimethylorthoacetate and 100 ml. of a 20% solution of propionic acid in benzene in 2 L. of benzene was heated for 24 hours, at 92°–93°C. The vapors were condensed and collected in a Dean-stark moisture receiver. After cooling, the resulting yellow solution was washed with 100 ml. of a 2N solution of sodium carbonate, then 3 × 100 ml. of water. Drying with magnesium sulfate and evaporation in vacuo gave 50.0 g. (95% yield) of crude methyl 5-(3-carbomethoxy-2-phenylthiazolidin-4-yl)-4-pentonoate. Gas chromatographic analysis showed a purity of 65–70%. If pure starting material is used instead in the process, no detectable impurities were detected in the final product.

Calcd for $C_{17}H_{21}NO_4S$ (335.42): Calcd: C, 60.88; H, 6.31; N, 4.18; S, 9.56. Found: C, 60.81; H, 6.24; N, 4.32; S, 9.15.

EXAMPLE 7

To a solution of 10.0 g. (0.03 mole) of 5-(3-carbomethoxy-2-phenylthiazolidin-4-yl)-4-pentenoate in 250 ml. of dry methanol cooled to 0°C. was added 9.57 g. (0.03 mole) of pyridine hydrobromide perbromide in one portion. After stirring for 5 minutes at 0°, the solution was refluxed for 1 hour, cooled, and evaporated. The residue was taken up in 200 ml. of methylene chloride and washed with 2 × 75 ml. of 1N hydrochloric acid. The organic phase was dried over sodium sulfate and evaporated to afford 11.7 g. of crude product containing the benzaldehyde by-product. This residue was chromatographed on 1 kg. of silica gel. eluting with benzene/ethyl acetate, 80:20. Benzaldehyde is first off the the column, followed eventually by 3.4 g. (0.0103 mole, 37%) of pure 3β-bromo-2α-carbomethoxyethyltetrahydrothiophene-4β-(R)-carbamic acid, methyl ester. The product was recrystallized from ethyl acetate/ petroleum ether to afford an analytical sample of the product melting at 139°–140°C.

Calcd for $C_{10}H_{16}BrNO_4S$ (326.214): Calcd: C, 36.82; H, 4.94; N, 4.29; S, 9.83; Br, 24.50. Found: C, 37.13; H, 5.22; N, 4.41; S, 9.79; Br. 24.47.

EXAMPLE 8

A solution of 5.5 g. (10.68 mmoles) of 3β-bromo-2α-carbomethoxyethyltetrahydrothiophene 4β-(R)-carbamic saturated methyl ester in 55 ml. of acetic acid, previously saturated with hydrogen bromide, was allowed to stand at 25° for 20 hours. The reaction mixture was evaporated to dryness and the residue was recrystallized from ethyl acetate (plus a trace of methanol) to afford 4.6 g. (10.32 mmoles, 79%) of pure 3-[4α-(S)-amino-3β-bromotetrahydrothiophene-2α-yl]propionic acid, methyl ester hydrobromide, m.p. 160°–161°C.

Calcd for $C_8C_{14}BrNO_2S\cdot HBr$ (349.10): Calcd: C, 27.53; H, 4.33; N, 4.01; Br, 45.78; S, 9.19. Found: C, 27.59; H, 4.22; N, 4.20; Br, 45.92; S, 9.14.

EXAMPLE 9

To a mixture of 1.1 g. (.134 mole) of sodium acetate anhydrous in 42 ml. of glacial acetic acid was added 4.2 g. (0.0120 mole) of 3-[4α-(S)-amino-3β-bromo-tetrahydrothiophene-2α-yl]-propionic acid, methyl ester hydrobromide. The reaction was heated to reflux and maintained at that temperature for 7 hours. The solvent was removed, and the residue partitioned between 50 ml. of 10% sodium bicarbonate and 200 ml. of methylene chloride. The aqueous phase was further extracted with 2 × 75 portions of methylene chloride. The organic phases were dried over sodium sulfate and evaporated to afford 2.70 g. (0.0114 mole, 96%) of 3α-amino-(S)-4β-bromotetrahydrothiophene-2α-propionic acid lactam. Recrystallization from ethyl acetate yielded an analytical sample of the product, m.p. 208°–209°C.

Calcd for $C_7H_{10}BrNOS$ (236.14): Calcd: C, 35.61; H, 4.27; N, 5.93; S, 13.58, Br, 33.84. Found: C, 35.75; H, 4.30; N, 5.87; S, 13.70; Br. 33.77.

EXAMPLE 10

A solution of 1.65 g. (7.02 mmoles) of 3α-amino-(S)-4β-bromotetrahydrothiophene-2α-propionic acid lactam in 33 ml. of dry dimethylformamide to which 1.0 g. (20.4 mmole) of lithium azide had been added was heated to 130°C. After 2.5 hours at that temperature, the reaction was cooled, concentrated, taken up in methylene chloride/water and transferred to a separatory funnel. The aqueous layer was extracted with 3 × 50 ml. portions of methylene chloride, the organic phases were combined, dried over sodium sulfate, and evaporated to yield 1.212 g of product mix. The residue was chromatographed on 12 thick layer silica gel plates, eluting with chloroform/methanol, 90:10. Two products were isolated. The desired 3α-amino-4α-(R)-azidotetrahydrothiophene-2α-propionic acid lactam was obtained as the less polar product in a yield of 0.227 g. (1.15 mmoles, 16%) at $R_f = 0.2$ and appeared as a colorless oil. The major product at $R_f = 0.1$ identified as cis-3-(S)-amino-2,3-dihydro-2-thiophene propionic acid lactam, was obtained in a yield 0.771 g. (4.97 mmoles, 71%).

EXAMPLE 11

A solution of 227 mg. (1.15 mmoles) of 3α-amino-4α-(R)-azidotetrahydrothiophene-2α-propionic acid lactam in 100 ml. of absolute ethanol was hydrogenated in the presence of 227 mg. of 10% Pd/C catalyst. After 16 hours at 25°/45 psi, the reaction was stopped, and the catalyst was filtered. Evaporation of the filtrate yielded 168 mg. (0.98 mmole, 85%) of crude 2α-propionic acid-delta-lactam. For purification, the product could be chromatographed on thick layer silica gel plates, eluting with chloroform/methanol/ammonium hydroxide. 89:10:1. The product gives a positive ninhydrin test and appears at $R_f$ 0.2. The yield of pure 2 is 115 mg. (0.67 mmole, 58%), m.p. 107°–109°. For analysis, a sample was recrystallized from ethyl acetate and found to have m.p. of 108°–109°C.

Calcd for $C_7H_{12}N_2OS$: Calcd: C, 48.81; H, 7.02; N, 16.26; S, 18.61. Found: C, 48.66; H, 7.00; N, 16.18; S, 18.57.

EXAMPLE 12

To a solution of 60 mg. (.349 mmole) of 3α-amino-4α-(R)-aminotetrahydrothiophene-2α-propionic acid-delta-lactam in 7 ml. of water was added 1.5 g. (7.93 mmole) of barium hydroxide monohydrate. The heterogeneous system was refluxed overnight. The suspended barium carbonate was filtered off and washed with water twice. The filtrate contains the desired intermediate 3α,4α-diaminotetrahydro-2α-(S)-thiophene propionic acid. After being concentrated to a volume of 10 ml., the filtrate was cooled to 0° and treated with gaseous phosgene until an acidic pH was observed. The reaction mixture was allowed to stand at 25° for 2.0 hours and then evaporated to dryness making sure no water remains. To the residue was added 20 ml. of dry methanol and 1 drop of concentrated sulfuric acid. The mixture was refluxed for 1.0 hours, cooled, and the suspended salts were filtered off and washed with methanol. The filtrate was concentrated and partitioned between water and 20% methanol/methylene chloride. The aqueous phase was further extracted with 5 × 50 ml. of 20 % methanol/methylene chloride. The organic phases were combined, dried over sodium sulfate, and evaporated to yield 36 mg. (0.157 mmole, 45%) pure all cis 2-oxohexahydrothieno[3,4-d]imidazole-4-(S)-propionic acid methyl ester, also known as d-bisnorbiotin methyl ester, m.p. 164°–166°. For analysis, a sample was recrystallized from ethyl acetate.

Calcd for $C_9H_{14}N_2O_3S$ (230.29): Calcd: C, 46.94; H, 6.13; N, 12.17; S, 13.92. Found: C, 47.04; H, 5.96; N, 12.16; S, 13.65.

EXAMPLE 13

A solution of 230 mg. (1 mmole) of all cis 2-oxohexahydrothieno[3,4-d]imidazole-4-(S)-propionic acid methyl ester (d-bisnorbiotin methyl ester) in 10 ml. of dry tetrahydrofuran was refluxed for 3.5 hours during which time a white solid separated. The reaction mixture was treated with 3 ml. of 1N hydrochloric acid and evaporated in dryness. The residue was recrystallized from water. Some lithium salts separate first and are filtered off. Concentration of the filtrate afforded a pure sample of all cis 2-oxohexahydrothieno[3,4-d]imidazole-4-(S)-propyl-3-ol, m.p. 189°–191°. The yield of first crop material is 75 mg. (0.37 mmole, 37%). More product is present in the mother liquors.

Calcd for $C_8H_{14}N_2O_2S$ (202.28); Calcd: C, 47.50; H, 6.98; N, 13.85; S, 15.85. Found: C, 47.52; H, 6.96; N, 13.76; S, 15.69.

EXAMPLE 14

A solution of 250 mg. (1.24 mmoles) of all cis 2-oxohexahydrothieno[3,4-d]imidazole-4-(S)-propyl-1-ol (d-bisnorbiotinol) in 5 ml. of glacial acetic acid which had been previously saturated with hydrogen bromide was heated to 100°C. After 0.5 hour, the solvent was removed and the residue was triturated with methanol at which point crystals of all cis d-3,4-(2'-keto-imidazolido)-1,2-trimethylene thiophanium bromide are separated. After one recrystallization from water/acetone. 180 mg. (0.68 mmole, 68%) of pure product were obtained as first crop material, m.p. 221°–222°C.

Calcd for $C_8H_{13}BrN_2OS$: Calcd: C, 36.24; H, 4.94; N, 10.56; S, 12.09; Br. 30.14. Found: C, 36.25; H, 4.82; N, 10.42; S, 12.33; Br. 29.91.

EXAMPLE 15

2.65 g. (10 mmoles) pulverized all cis d-3,4-(2'-ketoimidazolido)-1,2-trimethylene-thiophanium bromide are added to a warm solution of 0.46 g. (20 mmoles) of sodium in 10 cc. diethyl malonate. The mixture is stirred and heated for 6 hours in an oil bath of 120°C. Ice and chloroform are added; the chloroform layer is separated and washed 3 times with small amounts of ice water. The solution is concentrated in vacuo (oil bath of about 110°C.) and the residue *) is refluxed for 3 hours with a mixture of 12 g. barium hydroxide octahydrate, 20 cc. methanol and 50 cc. water. The mixture is diluted with 1–2 liters boiling water and the barium ions are precipitated with a slight excess of dilute sulfuric acid. The boiling mixture is filtered and concentrated in vacuo. The reaction product, d-biotin, thus obtained can be recrystallized from water and forms thin long plates melting with decomposition (loss of $CO_2$) around 190°C. The decomposition point varies greatly with the rate of heating.

*) Containing the d-3,4-(2'-ketoimidazolido)-2-(ω,ω-dicarbethoxybutyl)-thiophane.

Anal. Calcd for $C_{11}H_{16}O_5N_2S$: C, 45.82; H, 5.59. Found: C, 46.07; N, 5.32.

We claim:

1. A compound of the formula:

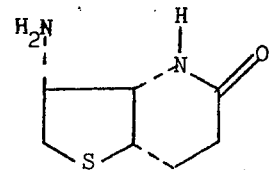

XII the racemates and optical antipodes thereof.

* * * * *